(12) United States Patent
Loria

(10) Patent No.: US 7,241,753 B2
(45) Date of Patent: Jul. 10, 2007

(54) METHOD OF TREATMENT OF PROSTATE CANCER

(76) Inventor: Roger M. Loria, 3219 Brooks Rd., Richmond, VA (US) 23277-4803

( * ) Notice: Subject to any disclaimer, the term of this patent is extended or adjusted under 35 U.S.C. 154(b) by 1030 days.

(21) Appl. No.: 09/794,531

(22) Filed: Feb. 26, 2001

(65) Prior Publication Data

US 2001/0046980 A1    Nov. 29, 2001

Related U.S. Application Data

(60) Provisional application No. 60/185,115, filed on Feb. 25, 2000.

(51) Int. Cl.
*A61K 31/56* (2006.01)

(52) U.S. Cl. .................................... 514/182
(58) Field of Classification Search ............... 514/182
See application file for complete search history.

(56) References Cited

U.S. PATENT DOCUMENTS

| | | |
|---|---|---|
| 4,628,052 A | 12/1986 | Peat |
| 4,898,694 A | 2/1990 | Schwartz et al. |
| 5,001,119 A | 3/1991 | Schwartz et al. |
| 5,028,631 A | 7/1991 | Schwartz et al. |
| 5,206,008 A | 4/1993 | Loria |
| 5,387,583 A | 2/1995 | Loria |
| 5,461,042 A | 10/1995 | Loria |
| 5,527,789 A | 6/1996 | Nyce |
| 5,641,768 A | 6/1997 | Loria |
| 5,714,481 A | 2/1998 | Schwartz et al. |
| 5,744,462 A | 4/1998 | Schwartz et al. |
| 5,763,433 A | 6/1998 | Morfin |
| 5,776,923 A | 7/1998 | Labrie |
| 5,798,347 A | 8/1998 | Labrie |
| 5,837,269 A | 11/1998 | Daynes et al. |
| 5,861,387 A | 1/1999 | Labrie |
| 5,912,240 A | 6/1999 | Loria |
| 5,922,728 A | 7/1999 | Panzeri et al. |
| 6,110,906 A | 8/2000 | Labrie et al. |

FOREIGN PATENT DOCUMENTS

| | | |
|---|---|---|
| WO | WO 94/23722 A | 10/1994 |
| WO | WO 95/10527 | 4/1995 |
| WO | WO97/37662 | * 10/1997 |
| WO | WO 97/37662 A | 10/1997 |
| WO | WO 98/31371 | 7/1998 |
| WO | WO 99/63973 | 12/1999 |
| WO | WO 99/63974 | 12/1999 |
| WO | WO 00/56757 | 9/2000 |
| WO | WO 01/23405 A2 | 4/2001 |

OTHER PUBLICATIONS

Berkow, Merck manual of Diagnosis and Therapy, 1992, 16th edition, p. 1750-1751.*
Rozhin et al., "Endocrine Steriod Sulfotransferases: Steriod Alcohol Sulfotransferase From Human Breat Carcinoma Cell Line MCF-7," *J. Steriod Biochem.*, 1986, pp. 973-979, vol. 25, No. 6.
Pasqualini, "Role of Androgens in Breast Cancer," *J. Steriod Biochem. Molec. Biol.*, 1993, pp. 167-172, vol. 45, Nos. 1-3.

* cited by examiner

*Primary Examiner*—San-Ming Hui
(74) *Attorney, Agent, or Firm*—Daryl D. Muenchau

(57) ABSTRACT

The present invention relates to the field of cancer, and in particular hormone dependent cancers including, but not limited to prostate, breast, endometrial, ovarian, thyroid, bone, and testis. The present invention also relates to the use of steroid analogues, and in particular analogues of $\Delta 5$-androstene-3-$\beta$, 17$\alpha$-diol, and its epimer $\Delta 5$-androstene-3-$\beta$, 17$\beta$-diol for the treatment and prevention of cancer.

72 Claims, No Drawings

METHOD OF TREATMENT OF PROSTATE CANCER

RELATED APPLICATIONS

This application claims priority to U.S. Provisional Patent Application No. 60/185,115, filed Feb. 25, 2000, hereby incorporated herein by reference in its entirety, including any drawings, tables, or figures.

FIELD OF THE INVENTION

The present invention relates to the field of cancer, and in particular hormone dependent cancers including, but not limited to prostate, breast, endometrial, ovarian, thyroid, bone, and testis. The present invention also relates to the use of steroid analogues, and in particular analogues of Δ5-androstene-3-β, 17α-diol, and its epimer Δ5-androstene-3-β, 17β-diol for the treatment and prevention of cancer.

BACKGROUND OF THE INVENTION

Prostate cancer is a common malignant tumor in the western world. In Sweden it ranks as the number one cause of death in malignant disease. No cure exists for advanced or metastasizing cases.

Standard treatment for prostate cancer involves surgical or pharmacological castration, i.e., androgen ablation, leading to remission in 70% of cases. Androgen ablation therapies typically used in the treatment of prostate cancer are designed to inhibit androgen receptor function, since the tumor is usually androgen-dependent. However, most cases relapse and become androgen-refractory disease within about 3 years. Life span is usually less than 1 year after hormone refractory relapse.

Immuno-therapy of prostate cancer by means of single cytokines has so far shown limited results. The response rate of patients to interferon-α is around 5% in hormone-refractory prostate cancer. The response to systemic IL-2 administration is difficult to distinguish from a no treatment control group.

The most promising results so far have been obtained by administration of TNF-α. However, systemic treatment with TNF-α results in side effects that significantly limit the clinical utility of TNF-α.

Δ5-Androstenediol (AED) is a naturally-occurring metabolite of dehydroepiandrosterone (DHEA), the most abundant product of the adrenal glands. AED may also arise from the metabolism of other steroids. AED exists in two epimeric forms: Δ5-androstene-3-β, 17α-diol (αAED) and Δ5-androstene-3-β, 17β-diol (βAED). Both are naturally occurring metabolites of dehydroepiandrosterone (DHEA). βAED has immunostimulating properties and immune upregulating properties. αAED has been shown to induce apoptosis in transformed cells in vitro. Apoptosis, or "programmed cell death," may be defined as a genetically determined destruction of cells from within due to activation of a stimulus or removal of a suppressing agent or stimulus.

In recent years there has been an increasing interest in the immunological effects of DHEA and other steroids. This has led to experiments where it has been shown that both DHEA in itself, and even more so βAED, protect against otherwise lethal infections. As this effect is not restricted to any single species of pathogenic microorganism, but encompasses RNA and DNA-type viruses, gram-positive and gram-negative bacteria, and parasites, it cannot be explained as an antibiotic effect.

Evaluation of the immune regulating effect of steroids has been accomplished using the methods first disclosed in U.S. Pat. No. 5,387,583, which is incorporated herein by reference.

Studies have shown that βAED treatment of lymphocytes previously stimulated with concanavalin A (con A), leads to increasing amounts of IL2, IL3 and TNF-α. Adding cortisone to a lymphocyte culture stimulated with con A leads to diminished quantities of cytokines IL-2 and IL-3. The effect of cortisone can be counteracted by adding βAED.

SUMMARY OF THE INVENTION

The present invention provides a method for treating cancer in a patient in need of such treatment comprising administering to said patient an effective amount of αAED, or an analogue thereof as defined below. Alternatively, the administration of αAED is followed by, or preceded by, administration of an effective amount of βAED, or an analogue thereof as defined below. Alternatively, the αAED and βAED are administered simultaneously. In one embodiment, the βAED is administered to the patient about 4–180 days after treatment of the patient with αAED. Yet another alternative of the present invention affords a method of treatment wherein the patient is treated with βAED alone.

In a first aspect, the invention features methods of treating prostate cancer in a patient in need of such treatment comprising administering a pharmaceutical formulation comprising a therapeutically effective amount of a compound of the formula (I):

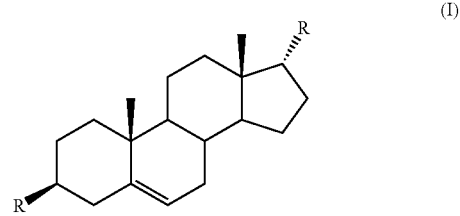

in an amount sufficient to arrest tumor growth, wherein R is independently selected from the group consisting of a hydroxyl, a protecting group, a $C_1$–$C_{30}$ ether (steroid-O-organic moiety), and a $C_1$–$C_{30}$ ester (steroid-O—C(O)-organic moiety or steroid-C(O)—O-organic moiety). Preferably, at least one R is —OH.

In typical embodiments, the compound is administered orally, topically, subcutaneously, parenterally, transdermally, mucosally, rectally, intranasally, via inhalation or insufflation. Also, the compound may be administered via a patch.

In other embodiments, the compound is applied to the site of the tumor or tumor bed or the compound is administered by installation into a wound.

In a second aspect, the invention features methods of treating prostate cancer in a patient in need of such treatment that further comprises the step of conjointly administering a pharmaceutical formulation comprising an immunostimulating-effective amount of a compound of the formula (II) and a compound of the formula (I), wherein the compound of formula (II) has the structure:

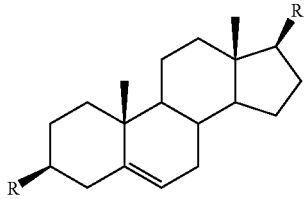

(II)

wherein either R is independently selected from the group consisting of a hydroxyl, a protecting group, a $C_1$–$C_{30}$ ether (steroid-O-organic moiety) and a $C_1$–$C_{30}$ ester (steroid-O—C(O)-organic moiety or steroid-C(O)—O-organic moiety). Preferably, each R is independently selected from the group consisting of a —OH and an ester.

In typical embodiments, the compound is administered orally, topically, subcutaneously, parenterally, transdermally, mucosally, rectally, intranasally, via inhalation or insufflation. Also, the compound may be administered via a patch.

In other embodiments, the compound is applied to the site of the tumor or tumor bed or the compound is administered by installation into a wound.

In a third aspect, the invention features methods of treating prostate cancer in a patient in need of such treatment as described in the first or second aspect further comprising conjoint administration of a therapeutic agent or a therapeutic treatment, wherein the therapeutic agent or the therapeutic treatment is selected from a therapeutically effective amount of one or more of the group consisting of: hydroxyflutamide, flutamide, leuprolide, megesterol, diethylstilbesterol, aminoglutethimide, spironolactone, tamoxifen, raloxifene, cyproterone acetate, bicalutamide, doxorubicin, cisplatin, estramustine phosphate, hydroxyurea, cyclophosphamide, cyclophosphamide dacarbazine (DITC), procarbazine, semustine (methyl-CCNU), methotrexate, 5-fluorouracil, streptozocinformestan, letrozole, anastrozole, toremifene, goserelin, leuprolide, vinorelbine, gemcitabine, paclitaxel, capecitabine, and radiation therapy, e.g. $^{60}CO$ or other or radiation treatments.

In a fourth aspect, the invention features methods of treating prostate cancer in a patient in need of such treatment as described in the first, second, or third aspects further comprising treatment with one or more of endocrine therapy, anti-androgen therapy, anti-estrogen therapy, cytotoxic agent, a cytotoxic treatment, a cytostatic agent, or surgery. Preferably, the cytotoxic treatment is radiation therapy or the surgery is selected from the group consisting of orchiectomy, lymphadenectomy, and lumpectomy.

In a fifth aspect, the invention features methods of treating prostate cancer in a patient in need of such treatment as described in the first, second, third, or fourth aspects wherein the prostate cancer is an androgen-resistant prostate cancer.

In a sixth aspect, the invention features methods of treating prostate cancer in a patient in need of such treatment as described in the first, second, third, fourth, or fifth aspects, wherein the R at the C-3 position is a $C_{1-15}$ alkyl moiety, a phenyl-$C_{1-4}$-alkyl moiety, a phenyl moiety, or a substituted analogue of any of these moieties, and optionally wherein 1, 2, 3 or 4 independently selected substituents are present, and wherein those substituents are optionally selected from the group consisting of: —O—, —S—, —NR'—, —NH—, —C(O)—, =O, =S, —N(R')$_2$, —NH$_2$, —C(O)OR', —C(O)OH, —OC(O)R', —O—C(O)—H, —OR', —OH, —SR', —SH, —NO$_2$, —CN, —SCN, —NHC(O)—, —C(O)NH—, —O—C(O)—, —C(O)—O—, —O—$C_{1-18}$ alkyl —S—$C_{1-18}$ alkyl, —C(O)—$C_{1-8}$ alkyl, —O—C(O)—$C_{1-8}$ alkyl, —C(O)—O—$C_{1-8}$ alkyl, —C(O)—O—$C_{1-8}$ alkyl-phenyl, phenyl, =N—, =N—OH, —OPO$_3$(R')$_2$, —OSO$_3$H$_2$, —F, —Cl, —Br or —I, and wherein each R' independently is —H or an independently selected protecting group for the atom to which it is attached, or both R's together comprise a protecting group. In typical embodiments, the substituted analogue comprises 1, 2, 3, 4 or more substituents that are independently selected from the group consisting of —OH, —O—, —C(O)—, —F, —Cl, —Br and —I.

In a seventh aspect, the invention features methods of preventing prostate cancer, slowing the progression of prostate cancer, inducing regression of a prostate cancer tumor or ameliorating one or more symptoms of prostate cancer in a patient having a benign prostrate hyperplasia or prostate cancer comprising delivering to the tissues of the patient or administering to the patient an effective amount of one or more compounds of the formula (I):

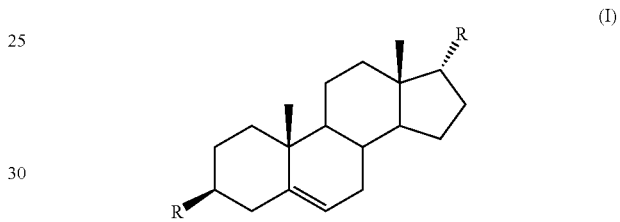

(I)

wherein R is as defined in the first aspect.

In some embodiments, the method of preventing prostate cancer further comprises treatment with endocrine therapy, anti-androgen therapy, anti-estrogen therapy, cytotoxic agent, a cytotoxic treatment, a cytostatic agent, radiation therapy, or surgery. Preferably, the surgery is selected from the group consisting of orchiectomy, lymphadenectomy, and lumpectomy.

In other embodiments, the method of preventing prostate cancer further comprises conjointly administering to the patient or delivering to the tissues of the patient an effective amount of a compound of formula (II), as defined in the second aspect, and a compound of formula (I).

In an eighth aspect, the invention features methods of treating a cancer or a pre-cancer, e.g. prostate cancer, in a patient in need of such treatment as described in the first, second, third, fourth, fifth, or seventh aspects, wherein R at the 17-position is a $C_{1-15}$ alkyl moiety, a phenyl-$C_{1-4}$ alkyl moiety, a phenyl moiety, or a substituted analogue of any of these moieties, and optionally wherein 1, 2, 3 or 4 independently selected substituents are present, and wherein those substituents are optionally selected from the group consisting of: —O—, —S—, —NR'—, —NH—, —C(O)—, =O, =S, —N(R')$_2$, —NH$_2$, —C(O)OR', —C(O)OH, —OC(O) R', —O—C(O)—H, —OR', —OH, —SR', —SH, —NO$_2$, —CN, —SCN, —NHC(O)—, —C(O)NH—, —O—C (O)—, —C(O)—O—, —O—$C_{1-18}$ alkyl —S—$C_{1-8}$ alkyl, —C(O)—$C_{1-8}$ alkyl, —O—C(O)—$C_{1-8}$ alkyl, —C(O)—O—$C_{1-8}$ alkyl, —C(O)—O—$C_{1-8}$ alkyl-phenyl, phenyl, =N—, =N—OH, —OPO$_3$(R')$_2$, —OSO$_3$H$_2$, —F, —Cl, —Br or —I, and wherein each R' independently is —H or an independently selected protecting group for the atom to which it is attached, or both R's together comprise a protecting group. In typical embodiments, the substituted analogue comprises 1, 2, 3, 4 or more substituents that are independently selected from the group consisting of —OH, —O—, —C(O)—, —F, —Cl, —Br and —I.

In a ninth aspect, the invention features using any one of the aspects described above in a method of treating, preventing, eradicating, slowing, or ameliorating (etc.) precancer, cancer, or metastatic cancer including a hormone dependent cancer. Typically, the hormone dependent cancer is selected from the group consisting of androgen-dependent cancer and estrogen-dependent cancer. Alternatively, the hormone dependent cancer is selected from the group consisting of prostate, breast, endometrial, ovarian, thyroid, bone, and testicular cancer. Alternatively, the cancer is not hormone dependent and includes, but is not limited to, any of those described herein.

With the foregoing, and other objects, advantages, and features of the invention that are apparent from the following disclosure, the nature of the invention may be more clearly understood by reference to the following detailed description of the invention, to the Examples, and to the appended claims.

DETAILED DESCRIPTION OF THE INVENTION

αAED has the capacity to stimulate apoptosis of cancer cells, while βAED has immune stimulation properties. This divergence in mechanisms allows the clinician the opportunity to tailor treatment to the individual patient or clinical situation. Thus, the clinician now has the option of formulating a treatment regimen utilizing either or both αAED and analogues and/or βAED and analogues depending on whether one wants to emphasize induction of apoptosis, immuno-stimulation, or a combination thereof.

The present invention provides a method for treating, or effecting prophylaxis in, a patient suffering from, or at risk of, cancer comprising administering to said patient a therapeutically effective, or prophylactically effective, amount of: 3β, 17α-Δ-5-androstenediol (αAED); its epimer, 3β, 17β-Δ-5-androstenediol (βAED); analogues of either or both, or a combination thereof. In the case of combination therapy, the administration of αAED or its analogues may be prior to, substantially simultaneously with, or after the administration of βAED or its analogues.

Definitions:

The following definitions are provided in order to facilitate the understanding of the instant invention.

As used herein, and unless stated otherwise, the term "patient" refers to any animal, particularly a mammal, e.g., a human, bovine, equine, canine, feline, or rodent. Generally the term contemplates such an animal bearing: (i) tumors, (ii) cancer cells, tissues or lesions, (iii) pre-cancerous cells, tissues, or lesions of any of these cancers or tumors, (iv) metastases of any of these cancers or tumors and (v) related disorders or symptoms thereof.

As used herein, and unless stated otherwise, the term "cancer", "tumor" or the like, includes, but is not limited to leukemia, polycythemia vera, lymphomas, multiple myeloma, Waldenstrom's macroglobulinemia, heavy chain disease, solid tumors, and any precancerous lesion or pre-cancerous tissue of any of these malignancies.

As used herein, and unless stated otherwise, the term "leukemia" or the like, includes, but is not limited to acute leukemias, e.g., acute lymphocytic leukemia, acute myelocytic leukemia (including myeloblastic, promyelocytic, myelomonocytic, monocytic, and erythroleukemia) and chronic leukemias, e.g., chronic myelocytic (granulocytic) leukemia and chronic lymphocytic leukemia.

As used herein, and unless stated otherwise, the term "lymphoma" or the like, includes, but is not limited to Hodgkin's disease non-Hodgkin's disease, and cutaneous T-cell lymphoma (e.g. mycosis fungoides, Sezary syndrome).

As used herein, and unless stated otherwise, the term "solid tumor" or the like, includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, pancreatic or gastric adenocarcinoma, human papilomavirus-associated cervical intraepithelial neoplasia, and hepatoma.

As used herein, and unless stated otherwise, the term "hormone-dependent" cancers, tumors, metastases, precancers or the like, includes, but is not limited to androgen-dependent and estrogen dependent. Examples of hormone dependent cancers include but are not limited to breast, prostate, endometrial, ovarian, thyroid, bone, testicular, vaginal carcinoma, cervical cancer, and osteosarcoma. Further examples of hormone-dependent cancer contemplated to be treated or prevented by the present invention can be found, for example, in *Cancer Medicine* Bast et al. eds. in Hormones and the Etiology of Cancer, Chapter 13, pg 195–206, hereby incorporated by reference herein in its entirety. An example of a pre-cancer is Benign prostatic hyperplasia (BPH).

As used herein, and unless stated otherwise, the term "AED analogue" means a molecule having the same steroidal tetracyclic structure, and the same pattern of substitution, but having different or modified substituents at the 3 and 17 positions. Thus, an analogue of AED contemplates AED wherein one or both of the hydroxy substituents is modified with a protecting group an ester, an ether, or is modified to a pharmaceutically acceptable salt, such as a halide or sulphate salt. AED analogues useful in the methods of the instant application can be identified by comparing the properties of the analogues with the properties of αAED and βAED described herein. Useful analogues will show activities similar to, or preferably better than, one or more of the activities observed with either αAED or βAED. These activities include, but are not limited to, immune up-regulation and inducing apoptosis in tumor cells. Examples of methods that can be used to identify useful analogues can be found, for instance, in Example 1, herein.

As used herein, and unless stated otherwise, terms such as "alkyl", "alkenyl moiety" and the like refers to a hydrocarbon containing up to about 20 carbon atoms in the form of normal, secondary, tertiary, cyclic, or mixed structures.

Examples include, but are not limited to, —CH$_3$, —CH$_2$CH$_3$, —CH$_2$CH$_2$CH$_3$, —CH(CH$_3$)$_2$—CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_2$CH$_3$, —CH(CH$_3$)CH$_2$CH$_2$CH$_3$, —CH(CH$_2$CH$_3$)$_2$, —C(CH$_3$)$_2$CH$_2$CH$_3$, —CH(CH$_3$)CH(CH$_3$)$_2$, —CH$_2$CH$_2$CH(CH$_3$)$_2$, —CH$_2$CH$_2$CH(CH$_3$)$_2$, —CH$_2$CH(CH$_3$)CH$_2$CH$_3$, —CH$_2$C(CH$_3$)$_3$, —CH$_2$CH$_2$CH$_2$CH$_2$CH$_3$, —CH(CH$_3$)CH$_2$CH$_2$CH$_3$, CH(CH$_2$CH$_3$)(CH$_2$CH$_2$CH$_3$), —C(CH$_3$)$_2$CH$_2$CH$_2$CH$_3$, —CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH(CH$_2$CH$_3$)CH(CH$_3$)$_2$, —C(CH$_3$)$_2$CH(CH$_3$)$_2$, —CH(CH$_3$)C(CH$_3$)$_3$, cyclopropyl, cyclobutyl, cyclopropylmethyl, cyclopentyl, cyclobutylmethyl, 1-cyclopropyl 1-ethyl, 2-cyclopropyl-1-ethyl, cyclohexyl, cyclopentylmethyl, 1-cyclobutyl-1-ethyl, 2-cyclobutyl-1-ethyl, 1-cyclopropyl-1-propyl, 2-cyclopropyl-1-propyl, 3-cyclopropyl-1-propyl, 2-cyclopropyl-2-propyl, and 1-cyclopropyl-2-propyl or an analogue of any of these that comprises 1, 2, 3 or more independently selected double (C=C) or triple (C≡C) bonds. Thus, the term alkyl contemplates saturated, unsaturated, and mixed or polyunsaturated systems; and thus the term includes alkanes, alkenes, alkynes, and combinations thereof.

As used herein, and unless stated otherwise, the term "organic moiety" means a hydrocarbon or mixed hydrocarbon moiety of up to about 30 carbons. Thus, the term contemplates, for example, alkyl moieties such as a C$_{1-5}$ alkyl moiety; an aryl moiety such as phenyl; a mixed alkyl-aryl moiety such as a phenyl-C$_{1-4}$-alkyl moiety; or substituted hydrocarbons comprising, e.g., about one to about four substituents wherein the substituents are selected from functional groups comprising one or more heteroatoms (e.g., O, N, S, P, Se), halides, or other non-toxic moieties. Thus, for example, the hydrocarbon substituents may be independently chosen from among: —O—, —S—, —NR'— (including —NH—), —C(O)—, =O, =S, —N(R')$_2$ (including NH$_2$), —C(O)OR' (including —C(O)OH), —OC(O)R' (including —O—C(O)—H), —OR' (including —OH), —SR' (including —SH), —NO$_2$, —CN, —NHC(O)—, —C(O)NH—, —O—C(O)—, —C(O)—O—, —O—C$_{1-4}$ alkyl, —S—C$_{1-4}$ alkyl, —C(O)—C$_{1-4}$ alkyl, —O—C(O)—C$_{1-4}$ alkyl, —C(O)—O—C$_{1-4}$ alkyl, —C(O)—O—C$_{1-4}$, —N=, =N—OH, —OPO$_3$(R')$_2$, —OSO$_3$H$_2$, wherein each R is selected from: H and an independently selected protecting group for the atom to which it is attached; and alkyl is C$_{1-8}$ alkyl, C$_{1-4}$ alkyl-aryl (e.g., benzyl), aryl, (e.g., phenyl) or C$_{1-4}$ alkyl-C$_{2-9}$ heterocycle. Substitutions are independently chosen. The substitutions listed above are substitutions that replace one or more carbon atoms, e.g., O or C(O), or one or more hydrogen atoms, e.g., —F, —Cl, —NH$_2$ or —OH.

As used herein, and unless stated otherwise, the term activities "similar to" or the like, means a quantitative measurement that is not necessarily statistically significant from the measurement obtained when either αAED or βAED are used in the assay. Alternatively, "similar to" can include values that are at least 1%, 2%, 5%, 7%, 10%, 15%, 20%, 25%, 30%, 40%, or 50% higher or lower than that observed with either αAED or βAED.

As used herein, and unless stated otherwise, the term activities "better than" or the like, means a quantitative measurement that is typically statistically significant from the measurement obtained when either αAED or βAED are used in the same assay. Depending on the assay and on the desired result, this may be a value that is either higher or lower than the value obtained when either αAED or βAED are used in the assay. The higher or lower value may be at least a 5%, 7%, 10%, 15%, 20%, 25%, 30%, 40%, 50%, 100%, 200% or greater change.

As used herein, and unless stated otherwise, the term "at least about 96 hours" means a time that is about 96 hrs, for example 84 hrs, 90 hrs, 102, or 114 hrs, and including longer intervals, for example 120 hrs, 144 hrs, or 168 hrs or even substantially longer such as 1, 2 or more weeks, or 1, 2 or more months. In alternative embodiments, the term can be stated as at least 48 hrs, at least 72 hrs, at least 96 hrs, at least 120 hrs, at least 144 hrs, at least 168 hrs, at least 1 week, at least 2 weeks, or at least a month, for example.

As used herein, and unless stated otherwise, the term "treating" and the like means administering the compounds described in the instant application to a patient in need of such treatment or delivering the compound(s) to the patient's tissues. Patients in need of treatment can be identified by methods well-known to those of skill in the art, for example by care givers, preferably physicians, nurses, nurses assistants, etc. Treatments include, but are not limited to, limiting or slowing progression, and/or metastases of malignancies and related disorders disclosed herein.

As used herein, and unless stated otherwise, the term "prophylactically", "preventing" and the like means administering the compounds described in the instant application to a patient at risk of contracting a disease or medical condition described in the instant application or who has a benign related condition such as benign prostate hyperplasia, and where the condition's development or progression is slowed or halted or a symptom is improved.

As used herein, and unless stated otherwise, the term "at risk of contracting" means a patient who has been identified as being exposed to or as having one or more risk factors associated with the onset of disease. These risk factors may be environmental, genetic, or biological. For example, for prostate and breast cancer risk factors would include age of the patient. Other risk factors include, but are not limited to, the presence of a precancer (e.g. BPH) or a family disposition to develop one of these conditions. Risk factors for the diseases described herein are known to one of ordinary skill in the art, such as physicians who typically diagnose and counsel patients.

As used herein, and unless stated otherwise, terms such as "ameliorate one or more symptoms" or the like mean to reduce the severity, or to improve, or to mask one or more symptoms of the disease. For example, symptom amelioration includes, but is not limited to, slowing or arresting tumor or tumor cell growth or reducing one or more symptoms such as pain, fever, or fatigue. This is a clinical determination within the sphere of the caregiver and the patient. Amelioration of symptoms may vary between subgroups of patients depending on a variety of factors including but not limited to their genetic background.

As used herein, and unless stated otherwise, the term "effective amount" means an amount of compound that when administered ameliorates one or more symptoms or prevents the onset of one or more symptoms of the disease. The effective amount for a particular patient and disease is a determination for the care giver.

As used herein, and unless stated otherwise, the term "eradicating" means removing or eliminating all detectable tumors. Detection of tumors is through means well known in the art and includes a gross anatomical perspective (e.g. removal of a lump) or a microscopic perspective (e.g. inability to detect cancerous cells through a biopsy or other appropriate means).

As used herein, and unless stated otherwise, the term "diminishing" means detectably decreasing the size of a tumor or detectably decreasing the number of cells comprising a tumor.

As used herein, and unless stated otherwise, the term "arresting the growth" means stopping a detectable increase in the size or in the number of cells of a tumor.

As used herein, and unless stated otherwise, the term "substantially decreasing the growth" means reducing the expected amount of increase in the growth of a tumor as measured by the increase in size or number of cells as compared to the growth of the tumor prior to treatment and/or the growth of control untreated tumors. By "substantially" is meant a detectable difference that is typically statistically significant by appropriate tests well known in the art.

As used herein, and unless stated otherwise, the term "conjoint administration" means administration either over the same period of time, for example over the same 2-week period, although not necessarily on the same days or at the same times. Alternatively, conjoint administration can include administration before or after administration of any of the compounds described herein, for example ending a day to a few days before (or after), or a week or more before (or after), or even a month or more before (or after) the start (or end) of administration of any the compounds described herein.

With regards to "conjoint administration" of αAED and βAED, it is meant the administration of αAED and βAED simultaneously, or substantially simultaneously (for example within about 30 minutes of one another). Alternatively, conjoint administration of αAED and βAED can include administering αAED prior to administering βAED to the patient. For example, βAED may be administered at least about 30 minutes; 1 hr; 2 hrs; 4 hrs; 6 hrs; 12 hrs; 24 hrs; 48 hrs; 72 hrs; 96 hrs; 120 hrs; 1 week; 2 weeks; 3 weeks; 1 month; 1.5 months; 2 months; 2.5 months; 3 months; 3.5 months; or 4 months after the administration of the αAED. Additionally, conjoint administration of αAED and βAED can include administering βAED prior to administering αAED. For example, the βAED may be administered at least about 30 minutes; 1 hr; 2 hrs; 4 hrs; 6 hrs; 12 hrs; 24 hrs; 48 hrs; 72 hrs; 96 hrs; 120 hrs; 1 week; 2 weeks; 3 weeks; 1 month; 1.5 months; 2 months; 2.5 months; 3 months; 3.5 months; or 4 months prior to the administration of the αAED.

As used herein, and unless stated otherwise, the term "excipient" means a component or an ingredient that is compatible with the compounds of formula I and/or formula II and not overly deleterious to the patient or animal to which the formulation is to be administered. As used here, "excipients" include liquids, such as benzyl benzoate, cottonseed oil, N,N-dimethylacetamide, a $C_{2-12}$ alcohol (e.g., ethanol), glycerol, peanut oil, a polyethylene glycol ("PEG"), vitamin E, poppyseed oil, propylene glycol, safflower oil, sesame oil, soybean oil and vegetable oil. Excipients, as used herein will optionally exclude chloroform, dioxane, vegetable oil, DMSO or any combination of these. Excipients comprise one or more components typically used in the pharmaceutical formulation arts, e.g., fillers, binders, disintegrants and lubricants.

Treatment Regimes

The present invention relates to the use of either or both of αAED and βAED, or analogues thereof, to treat or prevent breast cancer or prostate cancer or the related condition, benign prostatic hyperplasia (BPH), or to ameliorate one or more symptoms of any of these conditions. The invention includes treatment regimens comprising the administration of a pharmaceutical formulation comprising a therapeutically or prophylactically effective amount of one or more of αAED, analogues thereof, βAED, analogues thereof, or a combination thereof to a patient. The pharmaceutical formulation will further comprise conventional pharmaceutically acceptable excipients, diluents, carriers, and the like.

The treatment regimens of the present invention afford means for eradicating or diminishing breast cancers, prostate tumors or BPH, or arresting or substantially decreasing the growth thereof.

Generally, αAED is administered where there is a substantial or at least identifiable tumor or mass of cancerous cells. The conjoint administration of βAED can be used to boost the immune system to more effectively reduce or eliminate the tumor. Alternatively, the administration (e.g. systemically or locally) of βAED or βAED alone or jointly can be used where there is no identifiable tumor mass as where there are microtumors or wandering tumor cells within the body. Thus, the administration of αAED or βAED alone or jointly might be used where the progression of the prostate cancer is in a very early stage, or even for prophylactic purposes for patients particularly at risk. The administration of αAED or βAED alone or jointly could also be used post operatively or post treatment to prevent the spread of the tumor.

The active agents useful in the therapeutic regimens of the present invention are of the structure:

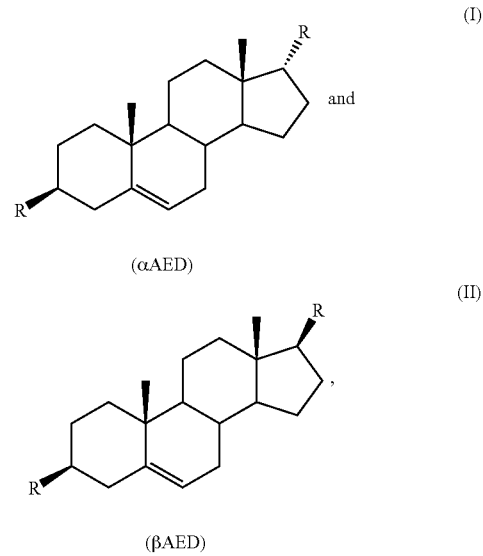

wherein each R is as defined above. Examples of ethers include O-alkyl of 1–30 carbons (e.g., —O—CH₃, —O—C₂H₅, —O—C₃H₇); O-phenylalkyl of 1–4 carbons (e.g., —O—CH₂—C₆H₅, —O—CH₂CH₂—C₆H₅,); or O-phenyl. Exemplary esters include —O—C(O)R₂, wherein R₂ is selected from among: H, alkyl of 1–30 carbons, phenylalkyl wherein the alkyl comprises 1–4 carbons (e.g., —C(O)—CH₂—C₆H₅, —C(O)—CH₂—CH₂—C₆H₅), and phenyl. Any phenyl moiety may further comprise 1, 2, or 3 moieties selected from hydroxy, carboxy of 1–4 carbons (e.g., —C(O)—OH, —CH₂C(O)—OH), halogens (e.g., —F, —Cl, —Br, or —I), alkoxy of 1–4 carbons (e.g, —O—CH₃, —OC$_2$H$_5$), alkyl of 1–4 carbons (e.g., —CH$_3$, —C$_2$H$_5$), wherein any alkyl may be a straight chain, branched chain, or wholly or partially cyclized or the alkyl may comprise 1, 2, 3 or more independently selected double or triple bonds.

Analogues of αAED and βAED having protecting groups can also be administered to the patient as a means of delivering αAED and/or βAED to target tissues. Thus, any reference herein to the use of αAED or βAED includes the optional use of one or more of their analogues described herein instead or in addition to the use of the parent compound itself. Acylation is a preferred method of protecting the compounds. Methods of making αAED, βAED, and analogues thereof are set forth in, e.g., U.S. Pat. No. 5,387,513 (αAED) and U.S. Pat. No. 2,521,586 (βAED), the contents of which are incorporated herein by reference. In some embodiments, R is —OH, or an —O-methyl keto radical to form an acetyl substituent. Similarly, analogues of αAED and βAED include pharmaceutically acceptable salts such as halides and sulphate salts.

When administered as described herein, these active agents selectively destroy prostate tumor cells, facilitating eradication of the tumor, or they can be used to arrest or inhibit growth of an androgen or estrogen resistant tumor, tumor cells or precancer, e.g. prostate tumor. As noted above, βAED has immunostimulating properties, while αAED has apoptotic properties. This divergence in mechanisms allows treatment to be tailored to the individual patient, by optionally utilizing immunostimulation along with αAED's capacity to induce apoptosis as necessary.

The capacity of αAED to effect benefits in the treatment of breast cancer, prostate cancer (or benign prostatic hyperplasia) or in the amelioration of one or more symptoms thereof is independent of the presence of the androgen receptor or the estrogen receptor in the target cells. This makes αAED a useful agent for use in patients with androgen-resistant or estrogen-resistant tumor cells or precancer, e.g. a prostate tumor. The medical practitioner of ordinary skill in the art will be able to readily modify the dose of each drug to effectively use the immuno-stimulating properties of βAED, along with the apoptotic properties of αAED, as required by each individual patient.

According to the present invention, αAED or βAED is administered in sufficient dosages to provide a blood concentration of about 5 to 10,000 nM of αAED or βAED. In general, an αAED dose of about 0.5 to about 300 mg/day for about 1 to about 4 days, generally about 0.5–250 mg/day, usually about 3–150 mg/day, will be suitable and efficacious for human therapeutic applications. αAED at a concentration of at least about 40 nM (e.g., about 40–200 nM), and usually about 50 nM is sufficient to inhibit the growth of prostate tumor cells in vitro.

When βAED is also used, it is generally administered at least about 30 minutes; 1 hr; 2 hrs; 4 hrs; 6 hrs; 12 hrs; 24 hrs; 48 hrs; 72 hrs; 96 hrs; 120 hrs; 1 week; 2 weeks; 3 weeks; 1 month; 1.5 months; 2 months; 2.5 months; 3 months; 3.5 months; or 4 months prior to the administration of the αAED. Alternatively, the βAED may be administered at least about 30 minutes; 1 hr; 2 hrs; 4 hrs; 6 hrs; 12 hrs; 24 hrs; 48 hrs; 72 hrs; 96 hrs; 120 hrs; 1 week; 2 weeks; 3 weeks; 1 month; 1.5 months; 2 months; 2.5 months; 3 months; 3.5 months; or 4 months after the administration of αAED. In one embodiment, βAED is administered at least about 4–60 days after the last day on which αAED was administered, e.g., about 7, 10, 14, 21, 28, 60, 90, 120, 150 or 180 days after administration of the last dose of αAED. In another embodiment, αAED is administered once or twice within a period of about 2 to about 14 days, followed about 7 to about 21 days later by administration of βAED daily for about 1 to about 10 days, using any of the dosages or dose ranges described herein.

The daily dosage of βAED is generally about 0.5–500 mg/day, usually about 3–400 mg/day (e.g., 0.5, 1, 2.5, 5, 15, 30, 60, 80, 100, 120, 150, 300, 400 or 500 mg/day), for human therapeutic applications. Doses of αAED or βAED are usually administered individually as single doses, but may also be administered individually as two or more subdivided doses. Alternatively, αAED or βAED are administered together in a single dose, or together as two or more subdivided doses.

αAED and βAED are administered by any conventional method, systemic or local. Suitable routes of administration include parenteral; topical; oral; rectal (e.g., suppositories, solutions for use as retention enemas and creams or jellies); buccal, sublingual (e.g., tablets or lozenges), intranasal or endotracheal (e.g., sprays, aerosols, or mists for inhalation or insufflation); mucosal; ocular; subcutaneous; and the like.

In some embodiments, αAED is administered locally, and can be effectively administered by injecting into or near the site of a breast tumor, a prostate tumor or a benign prostate growth. Alternatively, αAED is administered by applicator or in a spray directly onto tissue during surgery. The formulation may comprise a slow release composition to provide a source of αAED or βAED over a period of several days or a week or two.

In other embodiments, βAED is administered transepithelially, e.g., in a manner that brings the compound into contact with an epithelial layer in the patient. Preferred transepithelial routes of administration include topical, ocular (instillation into the eye), intranasal, inhalation, insufflation, buccal, perioral, subcutaneous, rectal, and any other mucosal route of administration.

The carrier system or vehicle used in a given instance will depend on the mode of administration. The formula I and formula II compounds are often lipophilic. Solvents and carriers for lipophilic steroids known in the art are appropriate for use in the compositions containing βAED or αAED or analogues thereof. Examples of such carriers or vehicles are glycols such as polypropylene glycol, polyethylene glycol, ethanol, DMSO and cyclodextrins (especially the amorphous cyclodextrins). Carriers such as cyclodextrins will pass through the buccal mucosa into the circulation easily. Other suitable vehicles include fatty acid esters of polyoxyethylene sorbitol (Tweens) or sorbitan (Spans) for preparation of emulsions. Other useful carriers include carboxymethylcellulose, benzyl benzoate, saline, and various sugars including glucose, fructose, and sucrose.

αAED or βAED may be delivered to or through the skin by any means, including subcutaneous or intradermal injection or topical application. One means of topical application is the use of skin patches impregnated with the active agent. This means of delivery is advantageous since it is non-invasive and easily administered by relatively unskilled care providers.

αAED and βAED can be formulated according to known methods to prepare pharmaceutically useful compositions such as by admixture with a pharmaceutically acceptable vehicle. Suitable vehicles and their formulation are described, for example, in Remington's Pharmaceutical Sciences (16th Ed., Osol, A. Ed., Mack Easton Pa. (1980)). To form a pharmaceutically acceptable composition suitable for effective administration, such compositions will contain an effective amount of αAED or βAED either alone or with one or more additional active agents, and a suitable amount of carrier vehicle.

Additionally, and as will be appreciated by one of ordinary skill in the art, conventional additives and excipients will be useful in formulating pharmaceutical compositions comprising the active agents described herein. Such excipients include buffers, antioxidants, stabilizers, diluents, and the like. Those additives and excipients will be dictated by the mode of administration selected.

For transdermal administration, patches for administration of αAED or βAED may be formulated as adhesive patches containing the active agent. For example, the patch may be a discoid in which a pressure-sensitive silicone adhesive matrix containing the active agent may be covered with a non-permeable backing. The discoid may either contain the active agent in the adhesive or may be attached to a support made of material such as polyurethane foam or gauze that will hold the active agent. In all instances, the area to which the patch is applied should be cleaned carefully before application. Patches may be prepared containing permeation enhancers such as cyclodextrin, butylated hydroxyanisole, or butylated hydroxytoluene.

For application directly to the skin, αAED or βAED may, for example, be dissolved in carrier material containing DMSO and alcohol, then applied to a patch or directly to epidermal tissues. For rectal administration, αAED or βAED may be administered by suppository, enema, or by application of creams, etc. Compositions of the invention may be administered by any method that will result in contact of the active agent with tissue of ectodermal origin.

The αAED or βAED may be administered to the mucosa of oral, pharyngeal or nasal cavity by tablet or lozenge. Additionally, when the active agent is administered to the mucosa of the oral cavity, it may be administered as a buccal tablet. Furthermore, administration to the oral-pharyngeal cavity and the nasal cavities may be by a spray.

When αAED or βAED or their analogues are administered orally, the active agents may be utilized more efficiently if the active agents are protected from destruction and absorption in the upper gastrointestinal tract. The active agents are most effective when the period of exposure to the mucosa of the intestinal tract is increased. Hence, tablets, caplets, or capsules containing the active agents in formulations to effect slow release in the intestine are used. Use of retention enemas for treatment is appropriate when the patient may have difficulty retaining compositions administered orally.

Compositions suitable for use in installation into wounds, for injection into tissues or for application to operative areas may be prepared by solubilizing the active agents of the invention in agents such as lipid solvents (for example, hydroxpropylene glycol) used to solubilize steroidal materials. Because the active agents are effective upon encountering tissue of ectodermal origin, they may, for example, be administered directly into the operative area as a spray or installation during surgical treatment of prostate malignancies. Compositions such as liposomes, cyclodextrin inclusion complexes or impregnated polymeric materials (including naturally occurring polymers or synthetic polymers) are particularly useful for such application.

The active agents, αAED and βAED, can be given in conjunction with other active agents, which may be given simultaneously or may be incorporated in compositions containing αAED or βAED. αAED or βAED can be given with anti-infective agents such as antibiotics, antiviral agents, antifungals, or antiparasitic agents, to potentiate the activity of these drugs by upregulating protective immune response. Antiviral agents include, for example, Dideoxyinosine, AZT, acyclovir, etc. Other active agents that may be combined with αAED or βAED include antiallergic medications such as epinephrine.

The agents taught herein may be used in conjunction with other active agents such as vinca alkaloids, nucleic acid inhibitors, platinum agents, interleukin-2, interferons, e.g. IFN-α, IFN-γ, TNF-α, alkylating agents, antimetabolites, corticosteroids, DNA intercalating agents, anthracyclines, ureas, and microtubule inhibitors. Examples of specific agents, in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

EXAMPLES

The following examples illustrate preferred embodiments of the invention; they should not be construed as limiting its scope in any way.

Example 1

In vitro experiments have shown an apoptotic effect of αAED in a myeloid cell line and in breast cancer cell lines. It has previously been shown that effects were not dependent on any androgenic or estrogenic effects. See U.S. Pat. No. 5,912,240.

The Dunning prostate cancer cell-line, AT-1, is a completely hormone-refractory tumor. It lacks measurable quantities of receptors for androgens as well as estrogens. As a result, the clinical behavior of this tumor is not influenced by the presence or absence of sex steroids. The doubling time of the tumor is 2.5 days, which makes it one of the most slow-growing of all hormone-refractory Dunning tumors. It has a low (less than 5%) tendency for metastasis. The Dunning tumors are suitable for evaluating immunologic experiments with prostate cancer as they grow in immunocompetent animals.

The experiments described below show the effect of αAED and βAED in vivo on the Dunning AT-1 tumor. The effects of αAED and βAED on Dunning, AT-1, hormone-refractory prostate cancer cell line in rats were investigated in two experiments with different tumor sizes as described below. The effects of αAED and βAED alone and in sequential combination were investigated. Biopsies from excised tumors where investigated microscopically using the TUNEL-technique. Tumor biopsies were investigated with immuno-cytochemistry and antibodies for macrophages and T-lymphocytes.

Materials and Methods.

Δ-5-androstene-3β, 17β-diol was purchased from Sigma Chemicals. Δ-5-androstene-3β, 17α-diol was purchased from Steraloid Company. Rat interferon and monoclonal antibodies to the markers ED-1 and CD3 were purchased from Novakemi Serotech Company. The apoptotic marker Apotag was used. PEG 400 was purchased from Sigma Chemicals.

Prostate tumor-bearing animals for the first experiment were purchased from Laboratory Animal Unit, Umea, Sweden. Male Copenhagen rats as well as male Copenhagen-Fisher rats for experiments one and two were purchased from Mollevang, Copenhagen, Denmark.

Experiment 1

In this experiment Dunning AT-1 tumor was passed through two Copenhagen-Fisher male rats and then transplanted in a single piece, approximately 10 mm³, which was placed subcutaneously on a third Copenhagen-Fisher male rat's dorsal side. Tumors were allowed to grow to approximately 17 mm in diameter before treatment started. Four groups of six rats each were used.

Group 1 animals received βAED in a mixture of absolute ethanol and PEG 400 1:1. βAED was given only on one occasion.

Group 2 animals received one intra-tumoral injection of 0.1 mL of complete Freund's adjuvant and βAED as above. Freund's complete adjuvant is used to potentiate immune reactivity and to trigger a T-cell response.

Group 3 animals received only complete Freund's adjuvant, 0.1 mL intra-tumorally.

Group 4 animals served as tumor-bearing controls.

Experiment 2

In the second experiment, rats were treated as in experiment 1, but tumor size was not allowed to exceed 10 mm in diameter. This experiment was made to further evaluate the influence of tumor size on the outcome of treatment.

Besides studying the effect of αAED as a single drug, a sequential treatment was used to test for an increased effect of a subsequent injection of βAED. Animals were divided in four groups:

Group 1 animals received a single injection of 80 mg βAED.

Group 2 and 3 animals received a single injection of 10 mg of αAED. Animals in Group 2 were sacrificed 96 hours after receiving αAED.

Group 3 animals received a single injection of βAED, 96 hours after receiving αAED.

Group 4 animals served as tumor-bearing controls.

Results:

First Experiment

Due to excessive tumor growth in the control group, rats had to be sacrificed after 3 weeks in Experiment 1.

Tumors were measured by slide caliper at the onset of experiment. This was repeated at the end of experiment when animals were sacrificed, tumors excised, and tumor weight was noted. The tumor sizes at the onset and end of the experiment are shown in Table 1.

At the end of experiment 1, mean tumor weight was 11.6 g in Group 1, 10.9 g in Group 2, 15.8 g in Group 3, and 19.2 g in controls (Group 4). Median weight, in the same order, was 10 g, 13 g, 16 g and 17 g. A p value less than 0.05 was considered as a statistically significant difference between groups. ANOVA between groups showed a p-value of 0.018. Difference in mean tumor weight between Group 1 (receiving βAED only) compared to control was statistically significant, with a p value=0.013. This was true also for the group receiving βAED and Freund's adjuvant compared to control, p=0.004. However, the difference between Group 3 receiving Freund's adjuvant only and controls was not significant.

TABLE 1

| Treatment | Tumor Diameter (mm) | Decrease in Tumor Size (mm) | Percent Reduction | p-value |
| --- | --- | --- | --- | --- |
| βAED | 11.6 | 7.6 | 39.58 | 0.013 |
| βAED + Freund's | 10.9 | 8.3 | 43.23 | 0.004 |
| Freund's | 15.8 | 3.4 | 17.71 | NS |
| Control | 19.2 | 0 | 0 | — |

Comparison of the results from Group 3 receiving Freund's adjuvant only with Group 4 controls using a Mann-Whitney (non-parametric) test likewise showed no significant difference, while both βAED vs. Control (p=0.013) and βAED and Freund's vs. Control (p=0.004) were statistically significant.

Second Experiment

In the second experiment, mean tumor weight in Group 1 receiving βAED was 2.9 g. In the control Group 4, mean tumor weight was 5.8 g. In Group 2 receiving αAED, tumor growth was arrested for at least 96 hours following treatment.

After animals had been sacrificed, freshly frozen tumor samples were examined for apoptosis using the TUNEL technique. In the animals treated with αAED and sacrificed after 96 hours there was no significant tumor growth observed macroscopically.

A clear retardation of tumor growth was seen in animals treated with βAED. αAED had a growth-inhibitory effect on tumor at the macroscopic level.

Example 2

Capsules of a formulation of αAED or βAED (or analogs as described herein) for oral administration may comprise 1 to 1000 mg αAED or βAED, 150 mg starch, and 5 mg magnesium stearate. The capsules are administered daily or twice a day to achieve a daily dosage of 1 to 1000, 2 to 500, or 5 to 50 mg per day, for example.

Example 3

A suspension may be prepared in multiple dose batches for administration subcutaneously. Each mL contains:

| | |
| --- | --- |
| αAED or βAED | 1 mg to 1000 mg |
| sodium citrate | 1 mg |
| polysorbate 80 | 1 mg |
| sorbitol solution | 0.5 mL |
| sterile water: | qs. 1 mL |

Similar amounts may be used in preparing a formulation containing AED analogues as described herein.

Example 4

A preparation for application to the skin or mucosa may be prepared in the following manner:

| Ingredient | % w/w |
| --- | --- |
| αAED or βAED | 0.1% to 10% |
| glyceryl monostearate | 3.0% |
| propylene glycol | 13.0% |
| Petrolatum | 83.9% to 73.9% |

Similar amounts may be used in preparing a formulation containing analogues described herein.

Example 5

A formulation for administration as a retention enema may be formulated in the following manner:

| Ingredient | w/w % |
| --- | --- |
| αAED or βAED | 4% to 25% |
| Propylene glycol | 96% to 75% |

Similar amounts may be used in preparing a formulation containing analogues described herein.

Example 6

A patch composed of a trilaminate of an adhesive matrix sandwiched between a non-permeable backing and a protective covering layer is prepared in the following manner:

To a pressure-sensitive silicone adhesive composition BIOPSIJM Q7-2920 (Dow Corning Corp., Midland, Mich., U.S.A.) in cyclohexane (50% w/v) is added sufficient αAED or βAED to provide a 0.5% to 25% αAED or βAED composition. The adhesive is applied to a polyester film to provide in successive layers about 2 mg of active agent per $cm^2$. The film containing the adhesive is then made into patches of 10 $cm^2$. Patches are covered with a protective layer to be removed before application of the patch. Patches may be prepared containing permeation enhancers such as cyclodextrin, butylated hydroxyanisole, or butylated hydroxytoluene. However, it should be remembered that the active agents of this invention are effective on application to the epidermal tissue. Similar amounts may be used in preparing a formulation containing analogues described herein.

Example 7

Preparation for instillation:

| Ingredient | % W/W |
| --- | --- |
| αAED or βAED | 0.01% to 10% |
| polypropylene glycol | 13.0% |
| Water | 86.5% to 76.6% |

Similar amounts may be used in preparing a formulation containing analogues described herein.

Example 8

Preparation for intravenous injection:

| Ingredient | Amount |
| --- | --- |
| αAED or βAED | 1 mg to 1 g |
| Ethanol | 5 mL |
| Phosphate buffered saline | Add to 1000 mL. |

Similar amounts may be used in preparing a formulation containing analogues described herein.

Example 9

Water, 100 mL, is mixed with 7 g hydroxypropyl-β-cyclodextrin and 1 mg to 1 g αAED or βAED. Fill ampules with the solution and sterilize. This preparation may be added to solutions for administration to the mucosa, for oral administration, or for parenteral administration. Similar amounts may be used in preparing a formulation containing analogues described herein.

Example 10

The cyclodextrin/αAED or βAED preparation is prepared as in Example 9, above. The material is freeze-dried and placed in sterile ampules. The resulting powder may be placed in vials. The contents of the vials may then be administered via insufflation. Alternatively, the contents of the vials may be dissolved or suspended for intravenous or topical application, including for infusion into a wound site. The contents may also be applied by spraying or sponging into the operative site such as the abdominal or thoracic cavity.

Example 11

The preparation of Example 10 is diluted with 100 mL water. The preparation may be sprayed into the abdominal cavity at the surgical sites during or after removal of a prostate malignancy. Similar amounts may be used in preparing a formulation containing analogues described herein.

Example 12

Capsules of a formulation of αAED or βAED for oral administration may be prepared by mixing 1 mg αAED or βAED (or more, e.g. at least up to 2 g), 15 mg starch and 5 mg magnesium stearate. The capsules may be administered twice a day to achieve a daily dosage of 1–50 mg/day or 2 to 100 mg/day, or 5 to 500 mg/day, or 10–1000 mg/day. Similar amounts may be used in preparing a formulation containing analogues described herein.

Example 13

A patch composed of a trilaminate of an adhesive matrix sandwiched between a non-permeable backing and a protective covering layer is prepared in the following manner:

To a pressure-sensitive silicone adhesive composition BIOPSA™ q7-2920 (Dow Corning Corporation, Midland, Mich., U.S.A.) in cyclohexane (50% w/v) is added sufficient αAED or βAED to provide a 0.5% to 25% αAED or βAED composition. The adhesive is applied to a polyester film to provide in successive layers about 2 mg of active agent per cm$^2$. Patches are covered with a protective layer which is removed before application. Similar amounts may be used in preparing a formulation containing analogues described herein.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

I claim:

1. A method of treating precancer, cancer, or metastatic cancer in a patient in need of such treatment comprising delivering to the tissues of said patient or administering to said patient a therapeutically effective amount of one or more compounds of formula (I):

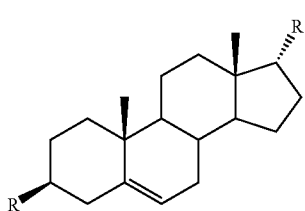

(I)

wherein each R is independently selected from the group consisting of a hydroxyl, a $C_1$–$C_{30}$ ether and a $C_1$–$C_{30}$ ester; and subsequently delivering to the tissues of said patient or administering to said patient a therapeutically effective amount of one or more compounds of formula (II):

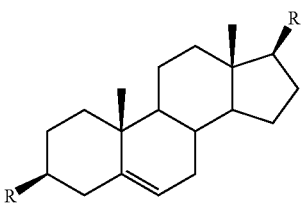

(II)

wherein each R is independently selected from the group consisting of a hydroxyl, a $C_1$–$C_{30}$ ether and a $C_1$–$C_{30}$ ester.

2. The method of claim 1, wherein at least one R in formula (I) is —OH.

3. The method of claim 1 wherein said one or more compounds of formula I and II are independently administered orally, topically, subcutaneously, parenterally, transdermally, mucosally, rectally, intranasally, via inhalation, via insufflation, via a patch, via application to the site of the tumor or tumor bed, via installation into a wound, by buccal, or by sublingual administration.

4. The method of claim 1, wherein said therapeutically effective amount of the compound of formula (I) slows or arrests the growth of said precancer, cancer or metastatic cancer.

5. The method of claim 1, wherein each R in formula (II) is independently selected from the group consisting of an —OH and an ester.

6. The method of claim 1, further comprising conjoint administration of a therapeutically effective amount of one or more therapeutic agents or therapeutic treatments selected from the group consisting of hydroxyflutamide, leuprolide, megesterol, diethylstilbesterol, aminoglutethimide, spironolactone, tamoxifen, raloxifene, cyproterone acetate, bicalutamide, doxorubicin, cisplatin, estramustine phosphate, hydroxyurea, cyclophosphamide, cyclophosphamide dacarbazine, procarbazine, semustine, methotrexate, 5-fluorouracil, streptozocin, formestan, letrozole, anastrozole, toremifene, goserelin, leuprolide, vinorelbine, gemcitabine, paclitaxel, capecitabine, and radiation therapy.

7. The method of claim 1, further comprising a conjoint treatment selected from the group consisting of endocrine therapy, anti-androgen therapy, anti-estrogen therapy, a cytotoxic agent, a cytotoxic treatment, a cytostatic agent, and surgery.

8. The method of claim 7, wherein said surgery is selected from the group consisting of orchiectomy, lymphadenectomy, and lumpectomy.

9. The method of claim 1, wherein said therapeutically effective amount of the compound of formula (II) stimulates the patient immune system.

10. The method of claim 1, wherein said precancer, cancer, or metastatic cancer is hormone-dependent.

11. The method of claim 10, wherein said precancer, cancer, or metastatic cancer is androgen dependent or estrogen dependent.

12. The method of claim 10, wherein said precancer, cancer, or metastatic cancer is selected from the group consisting of benign prostate hyperplasia, prostate cancer, breast cancer, endometrial cancer, ovarian cancer, thyroid cancer, bone cancer and testicular cancer.

13. The method of claim 12, wherein said cancer is androgen-resistant prostate cancer.

14. A method of treating precancer, cancer, or metastatic cancer in a patient in need of such treatment comprising delivering to the tissues of said patient or administering to said patient a therapeutically effective amount of one or more compounds of formula (I):

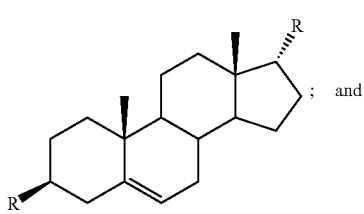

(I)

; and subsequently delivering to the tissues of said patient or administering to said patient a therapeutically effective amount of one or more compounds of formula (II):

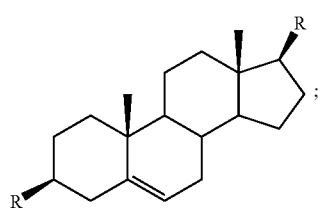

(II)

;

wherein the R at the C-3 position is selected from the group consisting of a $C_{1-15}$ alkyl moiety, a phenyl-$C_{1-4}$-alkyl moiety, a phenyl moiety, and a substituted analogue thereof, and wherein 1, 2, 3 or 4 independently selected substituents are present, and wherein said substituents are selected from the group consisting of —O—, —S—, —NH—, —C(O)—, =O, =S, —NH$_2$, —C(O)OH, —O—C(O)—H, —OH, —SH, —NO$_2$, —CN, —SCN, —NHC(O)—, —C(O)NH—, —O—C(O)—, —C(O)—O—, —O—$C_{1-18}$ alkyl, —S—$C_{1-8}$ alkyl, —C(O)—$C_{1-8}$ alkyl, —O—C(O)—$C_{1-8}$ alkyl, —C(O)—O—$C_{1-8}$ alkyl, —C(O)—O—$C_{1-8}$ alkyl-phenyl, phenyl, =N—, =N—OH, —OPO$_3$(H)$_2$, —OSO$_3$H$_2$, —F, —Cl, —Br and —I, and wherein the R at the C-17 position is independently selected from the group consisting of a hydroxyl, a $C_1$–$C_{30}$ ether and a $C_1$–$C_{30}$ ester.

15. The method of claim 14, wherein said compound of formula (II) has 3, 4 or more substituents that are independently selected from the group consisting of —OH, —O—, —F, —Cl, —Br and —I.

16. A method of treating precancer, cancer, or metastatic cancer in a patient in need of such treatment comprising delivering to the tissues of said patient or administering to said patient a therapeutically effective amount of one or more compounds of formula (I):

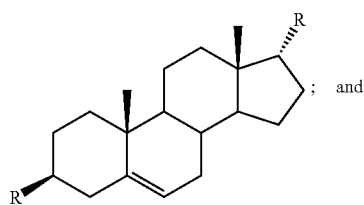

(I)

; and subsequently delivering to the tissues of said patient or administering to said patient a therapeutically effective amount of one or more compounds of formula (II):

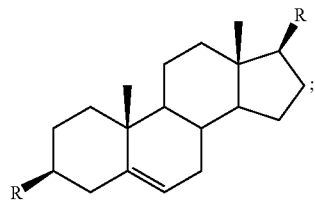

(II)

;

wherein the R at the C-3 position is independently selected from the group consisting of a hydroxyl, a $C_1$–$C_{30}$ ether and a $C_1$–$C_{30}$ ester, and wherein the R at the C-17 position is selected from the group consisting of a $C_{1-15}$ alkyl moiety, a phenyl-$C_{1-4}$ alkyl moiety, a phenyl moiety, and a substituted analogue thereof, and wherein 1, 2, 3 or 4 independently selected substituents are present, and wherein said substituents are selected from the group consisting of —O—, —S—, —NH—, —C(O)—, =O, =S, —NH$_2$, —C(O)OH, —O—C(O)—H, —OH, —SH, —NO$_2$, —CN, —SCN, —NHC(O)—, —C(O)NH—, —O—C(O)—, —C(O)—O—, —O—$C_{1-18}$ alkyl, —S—$C_{1-8}$ alkyl, —C(O)—$C_{1-8}$ alkyl, —O—C(O)—$C_{1-8}$ alkyl, —C(O)—O—$C_{1-8}$ alkyl, —C(O)—O—$C_{1-8}$ alkyl-phenyl, phenyl, =N—, =N—OH, —OPO$_3$(H)$_2$, —OSO$_3$H$_2$, —F, —Cl, —Br and —I.

17. The method of claim 16, wherein said compound of formula (II) has three or more substituents that are independently selected from the group consisting of —OH, —O—, —F, —Cl, —Br and —I.

18. The method of claim 1, wherein said one or more compounds of formula I or formula II are administered to said patient as part of a pharmaceutical formulation that further comprises one or more excipients.

19. The method of claim 1, wherein said one or more compounds of formula (II) are subsequently delivered to said patient after about 96 hours.

20. The method of claim 6, wherein said one or more therapeutic agents or therapeutic treatments are administered conjointly with said one or more compounds of formula (I).

21. The method of claim 6, wherein said one or more therapeutic agents or therapeutic treatments are administered conjointly with said one or more compounds of formula (II).

22. The method of claim 7, wherein said one or more therapeutic agents or therapeutic treatments are administered conjointly with said one or more compounds of formula (I).

23. The method of claim 7, wherein said one or more therapeutic agents or therapeutic treatments are administered conjointly with said one or more compounds of formula (II).

24. The method of claim 14, wherein said one or more compounds of formula (II) are subsequently delivered to said patient after about 96 hours.

25. The method of claim 14, wherein said one or more compounds of formula I and II are independently administered orally, topically, subcutaneously, parenterally, transdermally, mucosally, rectally, intranasally, via inhalation, via insufflation, via a patch, via application to the site of the tumor or tumor bed, via installation into a wound, by buccal, or by sublingual administration.

26. The method of claim 14, wherein said therapeutically effective amount of the compound of formula (I) slows or arrests the growth of said precancer, cancer or metastatic cancer.

27. The method of claim 14, further comprising conjoint administration of a therapeutically effective amount of one or more therapeutic agents or therapeutic treatments selected from the group consisting of hydroxyflutamide, leuprolide, megesterol, diethylstilbesterol, aminoglutethimide, spironolactone, tamoxifen, raloxifene, cyproterone acetate, bicalutamide, doxorubicin, cisplatin, estramustine phosphate, hydroxyurea, cyclophosphamide, cyclophosphamide dacarbazine, procarbazine, semustine, methotrexate, 5-fluorouracil, streptozocin, formestan, letrozole, anastrozole, toremifene, goserelin, leuprolide, vinorelbine, gemcitabine, paclitaxel, capecitabine, and radiation therapy.

28. The method of claim 27, wherein said one or more therapeutic agents or therapeutic treatments are administered conjointly with said one or more compounds of formula (I).

29. The method of claim 27, wherein said one or more therapeutic agents or therapeutic treatments are administered conjointly with said one or more compounds of formula (II).

30. The method of claim 14, further comprising a conjoint treatment selected from the group consisting of endocrine therapy, anti-androgen therapy, anti-estrogen therapy, a cytotoxic agent, a cytotoxic treatment, a cytostatic agent, and surgery.

31. The method of claim 29, wherein said one or more therapeutic agents or therapeutic treatments are administered conjointly with said one or more compounds of formula (I).

32. The method of claim 29, wherein said one or more therapeutic agents or therapeutic treatments are administered conjointly with said one or more compounds of formula (II).

33. The method of claim 30, wherein said surgery is selected from the group consisting of orchiectomy, lymphadenectomy, and lumpectomy.

34. The method of claim 14, wherein said therapeutically effective amount of the compound of formula (II) stimulates the patient immune system.

35. The method of claim 14, wherein said precancer, cancer, or metastatic cancer is hormone-dependent.

36. The method of claim 35, wherein said precancer, cancer, or metastatic cancer is androgen dependent or estrogen dependent.

37. The method of claim 35, wherein said precancer, cancer, or metastatic cancer is selected from the group consisting of benign prostate hyperplasia, prostate cancer, breast cancer, endometrial cancer, ovarian cancer, thyroid cancer, bone cancer and testicular cancer.

38. The method of claim 37, wherein said cancer is androgen-resistant prostate cancer.

39. The method of claim 14, wherein said one or more compounds of formula I or formula II are administered to said patient as part of a pharmaceutical formulation that further comprises one or more excipients.

40. The method of claim 16, wherein said one or more compounds of formula (II) are subsequently delivered to said patient after at least about 96 hours.

41. The method of claim 16, wherein said one or more compounds of formula I and II are independently administered orally, topically, subcutaneously, parenterally, transdermally, mucosally, rectally, intranasally, via inhalation, via insufflation, via a patch, via application to the site of the tumor or tumor bed, via installation into a wound, by buccal, or by sublingual administration.

42. The method of claim 16, wherein said therapeutically effective amount of the compound of formula (I) slows or arrests the growth of said precancer, cancer or metastatic cancer.

43. The method of claim 16, further comprising conjoint administration of a therapeutically effective amount of one or more therapeutic agents or therapeutic treatments selected from the group consisting of hydroxyflutamide, leuprolide, megesterol, diethylstilbesterol, aminoglutethimide, spironolactone, tamoxifen, raloxifene, cyproterone acetate, bicalutamide, doxorubicin, cisplatin, estramustine phosphate, hydroxyurea, cyclophosphamide, cyclophosphamide dacarbazine, procarbazine, semustine, methotrexate, 5-fluorouracil, streptozocin, formestan, letrozole, anastrozole, toremifene, goserelin, leuprolide, vinorelbine, gemcitabine, paclitaxel, capecitabine, and radiation therapy.

44. The method of claim 43, wherein said one or more therapeutic agents or therapeutic treatments are administered conjointly with said one or more compounds of formula (I).

45. The method of claim 43, wherein said one or more therapeutic agents or therapeutic treatments are administered conjointly with said one or more compounds of formula (II).

46. The method of claim 16, further comprising a conjoint treatment selected from the group consisting of endocrine therapy, anti-androgen therapy, anti-estrogen therapy, a cytotoxic agent, a cytotoxic treatment, a cytostatic agent, and surgery.

47. The method of claim 46, wherein said one or more therapeutic agents or therapeutic treatments are administered conjointly with said one or more compounds of formula (I).

48. The method of claim 46, wherein said one or more therapeutic agents or therapeutic treatments are administered conjointly with said one or more compounds of formula (II).

49. The method of claim 46, wherein said surgery is selected from the group consisting of orchiectomy, lymphadenectomy, and lumpectomy.

50. The method of claim 16, wherein said therapeutically effective amount of the compound of formula (II) stimulates the patient immune system.

51. The method of claim 16, wherein said precancer, cancer, or metastatic cancer is hormone-dependent.

52. The method of claim 51, wherein said precancer, cancer, or metastatic cancer is androgen dependent or estrogen dependent.

53. The method of claim 51, wherein said precancer, cancer, or metastatic cancer is selected from the group consisting of benign prostate hyperplasia, prostate cancer, breast cancer, endometrial cancer, ovarian cancer, thyroid cancer, bone cancer and testicular cancer.

54. The method of claim 53, wherein said cancer is androgen-resistant prostate cancer.

55. The method of claim 16, wherein said one or more compounds of formula I or formula II are administered to said patient as part of a pharmaceutical formulation that further comprises one or more excipients.

56. A method of treating precancer, cancer, or metastatic cancer in a patient in need of such treatment comprising delivering to the tissues of said patient or administering to said patient a therapeutically effective amount of one or more compounds of formula (I):

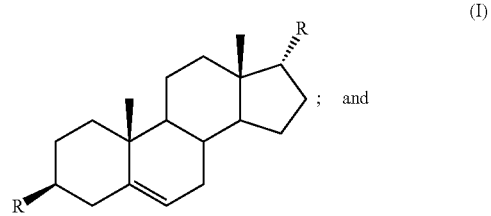

subsequently delivering to the tissues of said patient or administering to said patient a therapeutically effective amount of one or more compounds of formula (II):

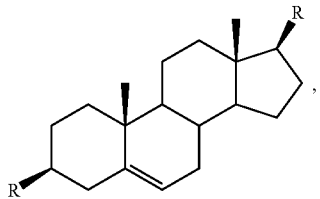

(II)

wherein each R is independently selected from the group consisting of a hydroxyl, an ether independently selected from the group consisting of O-alkyl of 1–30 carbons, O-phenylalkyl of 1–4 carbons, and O-phenyl, and an ester independently selected from the group consisting of O—C(O)H, O—C(O)-alkyl of 1–30 carbons, O—C(O)-phenylalkyl of 1–4 carbons, and O—C(O)-phenyl, wherein said phenyl independently comprises 0, 1, 2 or 3 moieties independently selected from the group consisting of halogen, hydroxy, carboxy of 1–4 carbons, alkoxy of 1–4 carbons, and alkyl of 1–4 carbons, wherein said alkyl is independently selected from the group consisting of straight chain, branched chain, and wherein said alkyl independently comprises 0, 1, 2, 3, or 4 independently selected double or triple bonds.

57. The method of claim 56, wherein said one or more compounds of formula (II) are subsequently delivered to said patient after about 96 hours.

58. The method of claim 56, wherein said one or more compounds of formula I and II are independently administered orally, topically, subcutaneously, parenterally, transdermally, mucosally, rectally, intranasally, via inhalation, via insufflation, via a patch, via application to the site of the tumor or tumor bed, via installation into a wound, by buccal, or by sublingual administration.

59. The method of claim 56, wherein said therapeutically effective amount of the compound of formula (I) slows or arrests the growth of said precancer, cancer or metastatic cancer.

60. The method of claim 56, further comprising conjoint administration of a therapeutically effective amount of one or more therapeutic agents or therapeutic treatments selected from the group consisting of hydroxyflutamide, leuprolide, megesterol, diethylstilbesterol, aminoglutethimide, spironolactone, tamoxifen, raloxifene, cyproterone acetate, bicalutamide, doxorubicin, cisplatin, estramustine phosphate, hydroxyurea, cyclophosphamide, cyclophosphamide dacarbazine, procarbazine, semustine, methotrexate, 5-fluorouracil, streptozocin, formestan, letrozole, anastrozole, toremifene, goserelin, leuprolide, vinorelbine, gemcitabine, paclitaxel, capecitabine, and radiation therapy.

61. The method of claim 60, wherein said one or more therapeutic agents or therapeutic treatments are administered conjointly with said one or more compounds of formula (I).

62. The method of claim 60, wherein said one or more therapeutic agents or therapeutic treatments are administered conjointly with said one or more compounds of formula (II).

63. The method of claim 60, further comprising a conjoint treatment selected from the group consisting of endocrine therapy, anti-androgen therapy, anti-estrogen therapy, a cytotoxic agent, a cytotoxic treatment, a cytostatic agent, and surgery.

64. The method of claim 63, wherein said one or more therapeutic agents or therapeutic treatments are administered conjointly with said one or more compounds of formula (I).

65. The method of claim 63, wherein said one or more therapeutic agents or therapeutic treatments are administered conjointly with said one or more compounds of formula (II).

66. The method of claim 56, wherein said surgery is selected from the group consisting of orchiectomy, lymphadenectomy, and lumpectomy.

67. The method of claim 56, wherein said therapeutically effective amount of the compound of formula (II) stimulates the patient immune system.

68. The method of claim 56, wherein said precancer, cancer, or metastatic cancer is hormone-dependent.

69. The method of claim 68, wherein said precancer, cancer, or metastatic cancer is androgen dependent or estrogen dependent.

70. The method of claim 68, wherein said precancer, cancer, or metastatic cancer is selected from the group consisting of benign prostate hyperplasia, prostate cancer, breast cancer, endometrial cancer, ovarian cancer, thyroid cancer, bone cancer and testicular cancer.

71. The method of claim 70, wherein said cancer is androgen-resistant prostate cancer.

72. The method of claim 56, wherein said one or more compounds of formula I or formula II are administered to said patient as part of a pharmaceutical formulation that further comprises one or more excipients.

* * * * *